US006861215B1

(12) United States Patent
Ali et al.

(10) Patent No.: US 6,861,215 B1
(45) Date of Patent: Mar. 1, 2005

(54) METHOD OF DIAGNOSING, MONITORING, AND STAGING PROSTATE CANCER

(75) Inventors: Shujath Ali, Santa Clara, CA (US); Susana Salceda, San Jose, CA (US); Yongming Sun, San Jose, CA (US); Robert Cafferkey, Mountain View, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/700,700

(22) PCT Filed: May 12, 1999

(86) PCT No.: PCT/US99/10548

§ 371 (c)(1),
(2), (4) Date: Nov. 20, 2000

(87) PCT Pub. No.: WO99/60162

PCT Pub. Date: Nov. 25, 1999

Related U.S. Application Data

(60) Provisional application No. 60/086,265, filed on May 21, 1998.

(51) Int. Cl.[7] ................................................ C12Q 1/68
(52) U.S. Cl. .................... 435/6; 435/91.1; 435/91.2; 435/94; 536/23.1; 536/24.3; 536/24.31
(58) Field of Search .......................... 435/6, 91.1, 91.2, 435/94; 536/23.1, 24.3, 24.31, 23.5; 530/350

(56) References Cited

U.S. PATENT DOCUMENTS

| 5,506,106 A | 4/1996 | Croce et al. |
| 5,674,682 A | * 10/1997 | Croce et al. ..................... 435/6 |
| 2002/0022248 A1 | 2/2002 | Xu et al. ................... 435/69.1 |

FOREIGN PATENT DOCUMENTS

| WO | WO 00/004968 A1 | 1/1999 |
| WO | WO 99/64594 | 12/1999 |
| WO | WO 00/04149 | 1/2000 |
| WO | WO 00/55174 A1 | 9/2000 |
| WO | WO 01/51633 A2 | 7/2001 |

OTHER PUBLICATIONS

Jansen, M et al, 1995, Pediatric Res, 37 (6): 681–686.*
Alberts et al. (Molecular Biology of the Cell, 3rd edition, 1994, p. 465).*
Shantz and Pegg (Int J of Biochem and Cell Biol., 1999, vol. 31, pp. 107–122).*
Mcclean and Hill (Eur J of Cancer, 1993, vol. 29A, pp. 2243–2248).*
Fu et al (EMBO Journal, 1996, vol. 15, pp. 4392–4401).*
Yokota, J et al (Oncogene, 1988, vol. 3, pp. 471–475).*
Zimmer (Cell Motility and the Cytoskeleton, 1991, vol. 20, pp. 325–337).*
Hell et al (Laboratory Investigation, 1995, vol. 73, pp. 492–496).*
Guo et al (Journal of Pharmacology and Experimental Therapeutics, 2002, vol. 300, pp. 206–212).*
Kibel, AS et al, 2000, J urol, 164(1):192–6.*
Zhau, HE, 1994, J Cell Biochem, Suppl 19: 208–216.*
Ren, C et al, 1998, Cancer Res, 58(6):1285–90.*
Gingrich, JR et al, 1996, Cancer res, 56(18): 4096–4102.*
Taber's cyclopedic medical dictionary, Clayton, T, ed. , 1989, Davis Co, Philadelphia, p. 231.*
Willis RA, et al, 1998, Int J mol med (Greece), 1(2): 379–86.*
Lai, E et al, 1991, Trends in Biochemical Sciences, V16, N11, P427–430.*
Deguchi. T et al. Detection of Micrometastatic Prostate Cancer Cells in the Bone Marrow of Patients with Prostate Cancer, British Journal of Cancer, 1997, vol. 75 No. 5, pp. 634–638.
An, G. et al. Cloning of Prostate–Specific Genes that are Suppressed in Metastatic Prostate Cancer by a PCR Southern Differential Hybridization Method. Proc. Am. Assoc. Can. Res., vol. 39, p. 208.
Abate–Shen et al., "Nkx3.1; Pten Mutant Mice Develop Invasive Prostate Adenocarcinoma and Lymph Node Metastases[1]", Cancer Research 2003 63 (14) :3886–3890.
Bierberich et al., "Prostate–specific and Androgen–dependent Expression of a Novel Homeobox Gene", J. Biol. Chem. 1996 271 (50) :31779–31782 reprinted as pp. 1–10.
He et al., "A Novel Human Prostate–Specific, Androgen–Regulated Homeobox Gene (NKX3.1) That Maps to 8p21, a Region Frequently Deleted in Prostate Cancer", Genomics 1997 43:69–77.
Herbrand et al., "Transcription factors Nkx3.1 and Nkx3.2 (Bapx1) play an overlapping role in sclerotomal development of the mouse", Mechanisms of Development 2002 117:217–224.
Kim et al., "Nkx3.1 Mutant Mice Recapitulate Early Stages of Prostate Carcinogenesis[1]", Cancer Research 2002 62:2999–3004.
Kim et al., "Cooperativity of Nkx3.1 and Pten loss of function in a mouse model of prostate carcinogenesis", Proc. Natl. Acad. Sci USA 2002 99 (5) :2884–2889 reprinted as pp. 1–10.
Prescott et al., "Isolation and Androgen Regulation of the Human Homeobox cDNA, NKX3.1", The Prostate 1998 35:71–80.
Sciavolino et al., "Tissue–Specific Expression of Murine Nkx3.1 in the Male Urogenital System", Developmental Dynamics 1997 209:127–138.

(List continued on next page.)

Primary Examiner—Susan Ungar
Assistant Examiner—Minh Tam Davis
(74) Attorney, Agent, or Firm—Licata & Tyrrell P.C.; Nathan P. Letts

(57) ABSTRACT

The present invention provides a new method for detecting, diagnosing, monitoring, staging and prognosticating prostate cancer.

1 Claim, No Drawings

OTHER PUBLICATIONS

NCBI Genbank Accession U80669 [gi:1732377] Dec. 10, 1996—Jun. 3, 1999 with Revision History.

He et al., "A Novel Human Prostate–Specific, Androgen–Regulated Homeobox Gene (NKX3.1) That Maps to 8p21, a Region Frequently Deleted in Prostate Cancer", Genomics 1997 43:69–77 XP–002084749.

López–Otín et al., "Breast and Prostate Cancer:An Analysis of Common Epidemiological, Genetic, and Biochemical Features", Endocrine Reviews 1998 19(4) :365–396 XP–002220464.

Olsson et al., "Reverse Transcriptase–Polymerase Chain Reaction Assays for Prostate Cancer", Urologic Clinics of North America 1997 24 (2) :367–377 XP002923009.

Prescott et al., "Isolation and Androgen Regulation of the Human Homeobox cDNA, NKX3.1", The Prostate 1998 35:71–80 XP–002084750.

Voeller et al., "Coding Region of NKX3.1, a Prostate–Specific Homeobox Gene on 8p21, Is Not Mutated in Human Prostate Cancers[1]", Cancer Research 1997 57:4455–4459 XP–002084751.

Database EMBL Human NKX3.1 mRNA, Dec. 17, 1996 Database accession No. HSU80669 XP002084746.

Database EMBL Human NKX3.1 gene, Oct. 15, 2002 Database accession No. NM_006167 XP–002223221.

* cited by examiner

US 6,861,215 B1

METHOD OF DIAGNOSING, MONITORING, AND STAGING PROSTATE CANCER

This application is national stage application of a 371 of PCT/US 99/10548 filed on May 12, 1999, which claims benefit of 60/086,265 filed on May 21, 1998.

FIELD OF THE INVENTION

This invention relates, in part, to newly developed assays for detecting, diagnosing, monitoring, staging, and prognosticating cancers, particularly prostate cancer.

BACKGROUND OF THE INVENTION

Cancer of the prostate is the most prevalent malignancy in adult males, excluding skin cancer, and is an increasingly prevalent health problem in the United States. In 1996, it was estimated that in the United States, 41,400 deaths would result from this disease, indicating that prostate cancer is second only to lung cancer as the most common cause of death in the same population. If diagnosed and treated early, when the cancer is still confined to the prostate, the chance of cure is significantly higher.

Treatment decisions for an individual are linked to the stage of prostate cancer present in that individual. A common classification of the spread of prostate cancer was developed by the American Urological Association (AUA). The AUA classification divides prostate tumors into four stages, A to D. Stage A, microscopic cancer within prostate, is further subdivided into stages A1 and A2. Sub-stage A1 is a well-differentiated cancer confined to one site within the prostate. Treatment is generally observation, radical prostatectomy, or radiation. Sub-stage A2 is a moderately to poorly differentiated cancer at multiple sites within the prostate. Treatment is radical prostatectomy or radiation. Stage B, palpable lump within the prostate, is further subdivided into stages B1 and B2. In sub-stage B1, the cancer forms a small nodule in one lobe of the prostate. In sub-stage B2, the cancer forms large or multiple nodules, or occurs in both lobes of the prostate. Treatment for both sub-stages B1 and B2 is either radical prostatectomy or radiation. Stage C is a large cancer mass involving most or all of the prostate and is further subdivided into two stages. In sub-stage C1, the cancer forms a continuous mass that may have extended beyond the prostate. In sub-stage C2, the cancer forms a continuous mass that invades the surrounding tissue. Treatment for both these sub-stages is radiation with or without drugs. The fourth stage is metastatic cancer and is also subdivided into two stages. In sub-stage D1, the cancer appears in the lymph nodes of the pelvis. In sub-stage D2, the cancer involves tissues beyond lymph nodes. Treatment for both these sub-stages is systemic drugs to address the cancer as well as pain.

However, current prostate cancer staging methods are limited. As many as 50% of prostate cancers initially staged as A2, B, or C are actually stage D, metastatic. Discovery of metastasis is significant because patients with metastatic cancers have a poorer prognosis and require significantly different therapy than those with localized cancers. The five year survival rates for patients with localized and metastatic prostate cancers are 93% and 29%, respectively.

Accordingly, there is a great need for increasingly sensitive methods for the staging of a cancer in a human to determine whether or not such cancer has metastasized and for monitoring the progress of a cancer in a human.

In the present invention, methods are provided for detecting, diagnosing, monitoring, staging and prognosticating cancers, particularly prostate cancer via seven (7) Prostate Specific Genes (PSG). The seven PSGs refer, among other things, to native proteins expressed by the genes comprising the polynucleotide sequences of any of SEQ ID NO: 1, 2, 3, 4, 5, 6, or 7. In the alternative, what is meant by the seven PSGs as used herein, means the native mRNAs encoded by the genes comprising any of the polynucleotide sequences of SEQ ID NO: 1, 2, 3, 4, 5, 6 or 7 or levels of the genes comprising any of the polynucleotide sequences of SEQ ID NO: 1, 2, 3, 4, 5, 6 or 7.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of prostate cancer in a patient which comprises measuring levels of PSG in a sample of cells, tissue or bodily fluid from the patient and comparing the measured levels of PSG with levels of PSG in preferably the same cells, tissue, or bodily fluid type of a control, wherein an increase in the measured PSG levels in the patient versus levels of PSG in the control is associated with prostate cancer.

Another object of the present invention is to provide a method of diagnosing metastatic prostate cancer in a patient which comprises measuring PSG levels in a sample of cells, tissue, or bodily fluid from the patient and comparing the measured PSG levels with levels of PSG in preferably the same cells, tissue, or bodily fluid type of a control, wherein an increase in measured PSG levels in the patient versus levels of PSG in the control is associated with a cancer which has metastasized.

Another object of the present invention is to provide a method of staging prostate cancer in a patient which comprises identifying a patient having prostate cancer, measuring levels of PSG in a sample of cells, tissues, or bodily fluid obtained from the patient, and comparing the measured PSG levels with levels of PSG in preferably the same cells, tissue or bodily fluid type of a control. An increase in measured PSG levels in the patient versus PSG levels in the control can be associated with a cancer which is progressing while a decrease or equivalent level of PSG measured in the patient versus the control can be associated with a cancer which is regressing or in remission.

Another object of the present invention is to provide a method of monitoring prostate cancer in a patient for the onset of metastasis. The method comprises identifying a patient having prostate cancer that is not known to have metastasized, periodically measuring levels of PSG in a sample of cells, tissues, or bodily fluid obtained from the patient, and comparing the measured PSG levels with levels of PSG in preferably the same cells, tissue, or bodily fluid type of a control, wherein an increase in measured PSG levels versus control PSG levels is associated with a cancer which has metastasized.

Yet another object of the present invention is to provide a method of monitoring the change in stage of prostate cancer in a patient which comprises identifying a patient having prostate cancer, periodically measuring levels of PSG in a sample of cells, tissue, or bodily fluid obtained from the patient, and comparing the measured PSG levels with levels of PSG in preferably the same cells, tissues, or bodily fluid type of a control wherein an increase in measured PSG levels versus the control PSG levels is associated with a cancer which is progressing and a decrease in the measured PSG levels versus the control PSG levels is associated with a cancer which is regressing or in remission.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays and methods, both quantitative and qualitative for detecting, diagnosing, monitoring, staging, and prognosticating cancers by comparing levels of PSG measured in a patient with levels of PSG in a control. What is meant by "levels of PSG" as used herein, means levels of the native protein expressed by the gene comprising the polynucleotide sequence of any of SEQ ID NO: 1, 2, 3, 4, 5, 6 or 7. In the alternative, what is meant by "levels of PSG" as used herein, is levels of the native mRNA encoded by the gene comprising any of the polynucleotide sequence of SEQ ID NO: 1, 2, 3, 4, 5, 6 or 7 or levels of the gene comprising any of the polynucleotide sequence of SEQ ID NO: 1, 2, 3, 4, 5, 6 or 7. Such levels are preferably measured in at least one of cells, tissues and/or bodily fluids, and includes determination of both normal and abnormal levels of PSGs. Thus, for instance, a diagnostic assay in accordance with the invention for diagnosing overexpression of PSG protein compared to control bodily fluids, cells, or tissue samples may be used to diagnose the presence of cancers, including prostate cancer. Any of the seven PSGs may be measured alone in the methods of the invention, all together or in various combinations of the seven PSGs.

By "control" it is meant a human patient without cancer and/or non cancerous samples from the patient, also referred to herein as a normal human control; in the methods for diagnosing or monitoring for metastasis, control may also include samples from a human patient that is determined by reliable methods to have prostate cancer which has not metastasized.

All the methods of the present invention may optionally include measuring the levels of other cancer markers as well as PSG. Other cancer markers, in addition to PSG, useful in the present invention will depend on the cancer being tested and are known to those of skill in the art. For example, simultaneous testing for increases in PSA as well as increases in PSG are also within the scope of the present invention and believed to provide a higher level of assurance that such cancer being tested is metastatic or the onset of metastasis has occurred.

Diagnostic Assays

The present invention provides methods -for diagnosing the presence of prostate cancer by analyzing for changes in levels of PSG in cells, tissues or bodily fluids compared with levels of PSG in cells, tissues or bodily fluids of preferably the same type from a normal human control, wherein an increase in levels of PSG in the patient versus the normal human control is associated with the presence of prostate cancer. Without limiting the instant invention, typically, for a quantitative diagnostic assay a positive result indicating the patient being tested has cancer is one in which cells, tissues, or bodily fluid levels of the cancer marker, such as PSG, are at least two times higher, and most preferably are at least five times higher, than in preferably the same cells, tissues, or bodily fluid of a normal human control.

The present invention also provides a method of diagnosing metastatic prostate cancer in a patient having prostate cancer which has not yet metastasized for the onset of metastasis. In the method of the present invention, a human cancer patient suspected of having prostate cancer which may have metastasized (but which was not previously known to have metastasized) is identified. This is accomplished by a variety of means known to those of skill in the art. For example, in the case of prostate cancer, patients are typically diagnosed with prostate cancer following traditional detection methods.

In the present invention, determining the presence of PSG in cells, tissues, or bodily fluid, is particularly useful for discriminating between prostate cancer which has not metastasized and prostate cancer which has metastasized.

Existing techniques have difficulty discriminating between prostate cancer which has metastasized and prostate cancer which has not metastasized and proper treatment selection is often dependent upon such knowledge.

In the present invention, the cancer marker levels measured in such cells, tissue, or bodily fluid are PSGs, and are compared with levels of PSG in preferably the same cells, tissue, or bodily fluid type of a normal human control. That is, if the cancer marker being observed is just PSG in serum, this level is preferably compared with the level of PSG in serum of a normal human patient. An increase in the PSG in the patient versus the normal human control is associated with prostate cancer which has metastasized.

Without limiting the instant invention, typically, for a quantitative diagnostic assay a positive result indicating the cancer in the patient being tested or monitored has metastasized is one in which cells, tissues, or bodily fluid levels of the cancer marker, such as PSG, are at least two times higher, and most preferable are at least five times higher, than in preferably the same cells, tissues, or bodily fluid of a normal patient.

Staging

The invention also provides a method of staging prostate cancer in a human patient.

The method comprises identifying a human patient having such cancer and analyzing a sample of cells, tissues, or bodily fluid from such patient for PSG. Then, the method compares PSG levels in such cells, tissues, or bodily fluid with levels of PSG in preferably the same cells, tissues, or bodily fluid type of a normal human control sample, wherein an increase in PSG levels in the patient versus the normal human control is associated with a cancer which is progressing and a decrease in the levels of PSG is associated with a cancer which is regressing or in remission.

Monitoring

Further provided is a method of monitoring prostate cancer in a human having such cancer for the onset of metastasis. The method comprises identifying a human patient having such cancer that is not known to have metastasized; periodically analyzing a sample of cells, tissues, or bodily fluid from such patient for PSG; and comparing the PSG levels in such cells, tissue, or bodily fluid with levels of PSG in preferably the same cells, tissues, or bodily fluid type of a normal human control sample, wherein an increase in PSG levels in the patient versus the normal human control is associated with a cancer which has metastasized.

Further provided by this invention is a method of monitoring the change in stage of prostate cancer in a human having such cancer. The method comprises identifying a human patient having such cancer; periodically analyzing a sample of cells, tissue, or bodily fluid from such patient for PSG; comparing the PSG levels in such cells, tissue, or bodily fluid with levels of PSG in preferably the same patient.

Monitoring such patient for onset of metastasis is periodic and preferably done on a quarterly basis. However, this may be more or less frequent depending on the cancer, the particular patient, and the stage of the cancer.

Assay Techniques

Assay techniques that can be used to determine levels of gene expression, such as PSG of the present invention, in a sample derived from a host are well-known to those of skill in the art. Such assay methods include radioimmunoassays, reverse transcriptase PCR (RT-PCR) assays, immunohistochemistry assays, in situ hybridization assays, competitive-binding assays, Western Blot analyses and ELISA assays. Among these, ELISAs are frequently preferred to diagnose a gene's expressed protein in biological fluids. An ELISA assay initially comprises preparing an antibody, if not readily available from a commercial source, specific to PSG, preferably a monoclonal antibody. In addition a reporter antibody generally is prepared which binds specifically to PSG. The reporter antibody is attached to a detectable reagent such as radioactive, fluorescent or enzymatic reagent, for example horseradish peroxidase enzyme or alkaline phosphatase.

To carry out the ELISA, antibody specific to PSG is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time PSG binds to the specific antibody attached to the polystyrene dish. Unbound sample is washed out with buffer. A reporter antibody specifically directed to PSG and linked to horseradish peroxidase is placed in the dish resulting in binding of the reporter antibody to any monoclonal antibody bound to PSG. Unattached reporter antibody is then washed out. Reagents for peroxidase activity, including a calorimetric substrate are then added to the dish. Immobilized peroxidase, linked to PSG antibodies, produces a colored reaction product. The amount of color developed in a given time period is proportional to the amount of PSG protein present in the sample. Quantitative results typically are obtained by reference to a standard curve.

A competition assay may be employed wherein antibodies specific to PSG attached to a solid support and labeled PSG and a sample derived from the host are passed over the solid support and the amount of label detected attached to the solid support can be correlated to a quantity of PSG in the sample.

Nucleic acid methods may be used to detect PSG mRNA as a marker for prostate cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e., gridding) can be used to both detect the expression of and quantitate the level of expression of that gene. In this approach, a cDNA encoding the PSG gene is fixed to a substrate. The substrate may be of any suitable type including but not limited to glass, nitrocellulose, nylon or plastic. At least a portion of the DNA encoding the PSG gene is attached to the substrate and then incubated with the analyte, which may be RNA or a complementary DNA (cDNA) copy of the RNA, isolated from the tissue of interest.

Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

The above tests can be carried out on samples derived from a variety of patients' cells, bodily fluids and/or tissue extracts (homogenates or solubilized tissue) such as from tissue biopsy and autopsy material. Bodily fluids useful in the present invention include blood, urine, saliva, or any other bodily secretion or derivative thereof. Blood can include whole blood, plasma, serum, or any derivative of blood.

EXAMPLES

The present invention is further described by the following examples. These examples are provided solely to illustrate the invention by reference to specific embodiments. These exemplifications, while illustrating certain specific aspects of the invention, do not portray the limitations or circumscribe the scope of the disclosed invention.

Example 1

PSGs

Searches were carried out and PSGs identified using the following Search Tools as part of the LIFESEQ® database available from Incyte Pharmaceuticals, Palo Alto, Calif.:

1. Library Comparison (compares one library to one other library) allows the identification of clones expressed in tumor and absent or expressed at a lower level in normal tissue.
2. Subsetting is similar to library comparison but allows the identification of clones expressed in a pool of libraries and absent or expressed at a lower level in a second pool of libraries.
3. Transcript Imaging lists all of the clones in a single library or a pool of libraries based on abundance.

Individual clones can then be examined using Electronic Northerns to determine the tissue sources of their component ESTs.

4. Protein Function: Incyte has identified subsets of ESTs with a potential protein function based on homologies to known proteins, Some examples in this database include Transcription Factors and Proteases. Some leads were identified by searching in this database for clones whose component ESTs showed disease specificity.

Electronic subtractions, transcript imaging and protein function searches were used to identify clones, whose component ESTs were exclusively or more frequently found in libraries from specific tumors. Individual candidate clones were examined in detail by checking where each EST originated.

TABLE 1

| SEQ ID NO: | Clone ID # | Gene ID # | |
|---|---|---|---|
| 1 | 1550426 | 244673 | Protein Function (Transcription Factors) |
| 2 | 1255804 | 14878 | Subsetting |
| 3 | 1808432 | 255819 | Subsetting |
| 4 | 3930803 | none | Subsetting |
| 5 | 645804 | 235032 | Subsetting |
| 6 | 1862352 | 221558 | Subsetting |
| 7 | 1450626 | 236019 | Subsetting |

Example 2

Measurement of SEQ ID NO:1; Clone ID # 1550426; Gene ID #244673 (pro101)

The example is carried out using standard techniques, which are well known and routine to those of skill in the art, except where otherwise described in detail. Routine molecular biology techniques of the following example are carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Relative Quantitation of Gene Expression

Real-time quantitative PCR with fluorescent Taqman probes is a quantitative detection system utilizing the 5'–3' nuclease activity of Taq DNA polymerase. The method uses an internal fluorescent oligonucleotide probe (Taqman) labeled with a 5' reporter dye and a downstream, 3' quencher dye. During PCR, the 5'–3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) is used as this endogenous control. To calculate relative quantitation between all the samples'studied, the target RNA levels for one sample are used as the basis for comparative results (calibrator). Quantitation relative to the "calibrator" is obtained using the standard curve method or the comparative method (User Bulletin #2: ABI PRISM 7700 Sequence Detection System).

To evaluate the tissue distribution, and the level of pro101 (SEQ ID NO:1) in normal and tumor tissue, total RNA was extracted from tumor and matched normal adjacent tissues and from unmatched tumor and normal tissues. Subsequently, first strand cDNA was prepared with reverse transcriptase and the polymerase chain reaction carried out using primers and Taqman probe specific to pro101 (SEQ ID NO:1). The results were obtained using the ABI PRISM 7700 Sequence Detector. The absolute numbers are relative levels of expression of pro101 (SEQ ID NO:1) compared to the calibrator.

The absolute numbers are depicted in the following Table 2 as relative levels of expression in 12 normal tissues of pro101 (SEQ ID NO:1) compared to kidney (calibrator). These RNA samples were generated by pooling samples from a particular tissue from different individuals.

TABLE 2

Relative levels of pro101 Expression in Pooled Samples

| Tissue | NORMAL |
|---|---|
| Brain | 1.2 |
| Heart | 2 |
| Kidney | 1 |
| Liver | 7.2 |
| Lung | 48.2 |
| Mammary | 2.5 |
| Prostate | 1418.4 |
| Spleen | 1.6 |
| Small | 1.9 |
| Testis | 57.3 |
| Thymus | 1.3 |
| Uterus | 7.6 |

The relative levels of expression in Table 2 show that for the PSG pro101 (SEQ ID NO:1) mRNA expression is more than 20 fold higher in the pool of normal prostate compared with the other 11 normal tissue pools analyzed. These results demonstrate that mRNA expression of the PSG is highly specific for prostate.

The tissues shown in Table 2 correspond to pools of samples from different individuals. The tissues shown in the following Table 3 were obtained from individuals and are not pooled. Hence the values for mRNA expression levels shown in Table 2 cannot be directly compared to the values shown in Table 3.

The absolute numbers in Table 3 are relative levels of expression of pro101 (SEQ ID NO:1) compared to kidney (calibrator), in 60 pairs of matching samples. Each matching pair contains the cancer sample for a particular tissue and the normal adjacent sample for that same tissue, from the same individual. The results from 3 unmatched ovary tumor, 3 unmatched normal ovary, 1 unmatched mammary tumor and 1 unmatched normal mammary gland are also shown.

TABLE 3

Relative Levels of pro101 Expression in Individual Samples

| TISSUE | CANCER | MATCHING | UNMATCHED |
|---|---|---|---|
| Prostate 1 | 103.9 | 0 | |
| Prostate 2 | 2219 | 84.2 | |
| Prostate 3 | 5048.2 | 3623.6 | |
| Prostate 4 | 11052.3 | 2029.4 | |
| Prostate 5 | 229.1 | 41.1 | |
| Prostate 6 | 57.9 | 25.3 | |
| Prostate 7 | 58.5 | 57.069 | |
| Prostate 8 | 1074.6 | 610.8 | |
| Prostate 9 | 32.7 | 79.3 | |
| Prostate 10 | 15.8 | 2.09 | |
| Prostate 11 | 436.4 | 438 | |
| Prostate 12 | 49.5 | 59.3 | |
| Prostate 13 | 128 | 56 | |

TABLE 3-continued

Relative Levels of pro101 Expression in Individual Samples

| TISSUE | CANCER | MATCHING | UNMATCHED |
|---|---|---|---|
| Bladder 1 | 0 | 0 | |
| Bladder 2 | 0 | 0 | |
| Bladder 3 | 0.7 | 0 | |
| Colon 1 | 0 | 0 | |
| Colon 2 | 0 | 0 | |
| Colon 3 | 0 | 0 | |
| Colon 4 | 3.3 | 1.9 | |
| Colon 5 | 0.1 | 0.8 | |
| Colon 6 | 0 | 0 | |
| Lung 1 | 0 | 0 | |
| Lung 2 | 0.5 | 1.6 | |
| Lung 3 | 1.4 | 2.1 | |
| Lung 4 | 0 | 0 | |
| Lung 5 | 0 | 0 | |
| Kidney 1 | 0 | 0 | |
| Kidney 2 | 0 | 0 | |
| Kidney 3 | 0 | 0 | |
| Kidney 4 | 0 | 0 | |
| Liver 1 | 1.5 | 5.7 | |
| Liver 2 | 26.9 | 7.9 | |
| Liver 3 | 0 | 0 | |
| Pancreas 1 | 0.9 | 0.9 | |
| Pancreas 2 | 3 | 0 | |
| Pancreas 3 | 0 | 0 | |
| Pancreas 4 | 0 | 0 | |
| Pancreas 5 | 0 | 0 | |
| Stomach 1 | 0 | 0 | |
| Stomach 2 | 0 | 0 | |
| Stomach 3 | 0 | 0 | |
| Stomach 4 | 0 | 0 | |
| Stomach 5 | 0 | 0 | |
| Sm Int 1 | 0 | 0 | |
| Sm Int 2 | 0 | 0 | |
| Testis 1 | 0 | 0 | |
| Mammary 1 | 4 | 0 | |
| Mammary 2 | 5.6 | 0 | |
| Mammary 3 | 0.5 | 0 | |
| Mammary 4 | 0.4 | 0 | |
| Mammary 5 | 0.5 | | |
| Mammary 6 | | | 0 |
| Endo 1 | 1.6 | 7.6 | |
| Endo 2 | 0 | 0 | |
| Endo 3 | 0 | 0 | |
| Endo 4 | 0.3 | 0.2 | |
| Endo 5 | 5.8 | 5 | |
| Uterus 1 | 0 | 0 | |
| Uterus 2 | 0 | 0 | |
| Uterus 3 | 0 | 0 | |
| Uterus 4 | 2.2 | 2.6 | |
| Ovary 1 | 1.4 | | |
| Ovary 2 | | | 11.6 |
| Ovary 3 | 1.5 | | |
| Ovary 4 | | | 22.9 |
| Ovary 5 | 0 | | |
| Ovary 6 | | | 1.8 |

Among 128 samples in Table 3 representing 14 different tissues, the higher levels of expression are consistently in prostate tissues. These results confirm the tissue specificity results obtained with normal samples shown in Table 2. Table 2 and Table 3 represent a combined total of 140 samples in 18 human tissue types. Sixty-eight samples representing 13 different tissue types excluding prostate had no detected pro101 mRNA (Table 3). In 4 tissues (stomach small intestine kidney and testis) no pro101 (SEQ ID NO:1) mRNA was detected for any sample tested from individuals (Table 3). Expression of this PSG was detected in testis in the pooled normal sample (Table 3). The median expression in prostate cancer samples in Table 3 is 166.5 units. Excluding vary 4 (Normal), only 1 sample in Table 3, Liver 2 (Cancer), is greater than 10% of this value.

Comparisons of the level of mRNA expression in prostate tumor samples and the normal adjacent tissue from the same individuals are also shown in Table 3. The PSG pro101 (SEQ ID NO:1) is expressed at higher levels in 9 of 13 (69%) prostate cancer tissues (Prostate 1, 2, 3, 4, 5, 6, 8, 10 and 13) compared with the corresponding normal adjacent tissue. The level of expression of this PSG is lower in prostate tumor compared to normal adjacent tissue in two samples (Prostate 9 and 12). Equivalent levels of expression were detected in two matched samples (Prostate 7 and 11). Previous mRNA expression analysis for genes coding for the diagnostic markers PSA and PLA2 showed higher expression of the mRNA in 40% to 80% of the tumor samples compared to matching normal adjacent tissue. Higher expression in the tumor sample compared to the corresponding normal adjacent tissue is observed for Bladder 3, Colon 4, Liver 2, Pancreas 2, Endometrium 5 and. Mammary 1, 2 and 3. Higher expression in the normal adjacent samples is observed for Colon 5, Lung 2, Lung 3, Liver 1, Endometrium 1 and Uterus 4. However, the levels detected are in most cases comparable amongst the different tissues and low compared to levels found in most prostate tissues.

The high level of tissue specificity, plus the mRNA overexpression in 9 of 13 of the prostate tumor samples tested compared to the normal adjacent tissues are believed to make the PSG, pro101 (SEQ ID NO:1) a good diagnostic marker for detection of prostate cancer using mRNA.

What is claimed is:

1. A method for detecting the presence of prostate cancer in a patient comprising:

(a) measuring the level of PSG in a sample of prostate cells or prostate tissue or blood, plasma, serum or urine obtained from the patient; and (b) comparing the measured level of PSG with the level of PSG in a sample of prostate cells or prostate tissue or blood, plasma, serum or urine obtained from a normal control, wherein an increase in the measured level of PSG in the patient versus the PSG level in the normal control is indicative of the presence of prostate cancer and wherein the PSG comprises SEQ ID NO:1.

* * * * *

SEQUENCE LISTING

```
<160> NUMBER OF SEQ ID NOS: 7

<210> SEQ ID NO 1
<211> LENGTH: 1936
<212> TYPE: DNA
<213> ORGANISM: Homo sapiens
<220> FEATURE:
<221> NAME/KEY: misc_feature
<222> LOCATION: (106)..(106)
<223> OTHER INFORMATION: n=a, c, g or t
```

```
<220> FEATURE:
<221> NAME/KEY: misc_feature
<222> LOCATION: (455)..(455)
<223> OTHER INFORMATION: n=a, c, g or t
<220> FEATURE:
<221> NAME/KEY: misc_feature
<222> LOCATION: (459)..(459)
<223> OTHER INFORMATION: n=a, c, g or t
<220> FEATURE:
<221> NAME/KEY: misc_feature
<222> LOCATION: (468)..(468)
<223> OTHER INFORMATION: n=a, c, g or t
<220> FEATURE:
<221> NAME/KEY: misc_feature
<222> LOCATION: (1541)..(1541)
<223> OTHER INFORMATION: n=a, c, g or t
<220> FEATURE:
<221> NAME/KEY: misc_feature
<222> LOCATION: (1908)..(1908)
<223> OTHER INFORMATION: n=a, c, g or t

<400> SEQUENCE: 1
aatggtatgc caacttaagt atttacaggg tggcccaaat agaacaagat gcactcgctg      60
tgattttaag acaagctgta taaacagaac tccactgcaa gagggngggc cgggccagga     120
gaatctccgc ttgtccaaga caggggccta aggagggtct ccacactgct gctagggct      180 gttgcatttt tttattagta gaaagtggaa aggcctcttc tcaactttt tcccttgggc      240 tggagaattt agaatcagaa gtttcctgga gttttcaggc tatcatatat actgtatcct     300
gaaaggcaac ataattcttc cttccctcct tttaaatttt tgtgttcctt tttgcagcaa     360
ttactcacta aagggcttca ttttagtcca gattttagt ctggctgcac ctaacttatg     420
cctcgcttat ttagcccgag atctggtctt ttttntgtnt ttttttttntt tccgtctccc     480 caaagcttta tctgtcttga ctttttaaaa agtttgggg gcagattctg aattgggcta     540
aaagacatgc attttaaaa ctaggcaact tcttatttct ttccttaaa aatacatagc     600 attaaatccc aaatcctatt taaagacctg acagcttgag aaggtcacta ctgcattat     660 aggaccttct ggtggttctg ctgttacgtt tgaagtctga caatccttga gaatctttgc     720
atgcagagga ggtaagaggt attggatttt cacagaggaa gaacacagcg cagaatgaag     780
ggccaggctt actgaggctg tccagtggag ggctcatggg tgggacatgg aaaagaaggc     840
agcctaggcc ctggggagcc cagtccactg agcaagcaag ggactgagtg agccttttgc     900
aggaaaaggc taagaaaaag gaaaaccatt ctaaaacaca acaagaaact gtccaaatgc     960
tttgggaact gtgtttattg cctataatgg gtcccccaaaa tgggtaacct agacttcaga    1020
gagaatgagc agagagcaaa ggagaaatct ggctgtcctt ccattttcat tctgttatct    1080
caggtgagct ggtagagggg agacattaga aaaaatgaa acaacaaaac aattactaat    1140
gaggtacgct gaggcctggg agtctcttga ctccactact taattccgtt tagtgagaaa    1200
cctttcaatt ttcttttatt agaagggcca gcttactgtt ggtggcaaaa ttgccaacat    1260
aagttaatag aaagttggcc aatttcaccc cattttctgt ggtttgggct ccacattgca    1320
atgttcaatg ccacgtgctg ctgacaccga ccggagtact agccagcaca aaaggcaggg    1380
tagcctgaat tgcttctgc tctttacatt tcttttaaaa taagcattta gtgctcagtc    1440
cctactgagt actcttctc tcccctcctc tgaatttaat tctttcaact tgcaatttgc    1500
aaggattaca catttcactg tgatgtatat tgtgttgcag ngaaaagaaa aaagtgtctt    1560 tgttttaaaat tacttggttt gtgaatccat cttgcttttt ccccattgga actagtcatt    1620
aacccatctc tgaactggta gaaaaacatc tgaagagcta gtctatcagc atctgacagg    1680
```

-continued

| | |
|---|---|
| tgaattggat ggttctcaga accatttcac ccagacagcc tgtttctatc ctgtttaata | 1740 |
| aattagtttg ggttctctac atgcataaca aaccctgctc caatctgtca cataaaagtc | 1800 |
| tgtgacttga agtttagtca gcaccccccac caaactttat ttttctatgt gttttttgca | 1860 |
| acatatgagt gttttgaaaa taaagtaccc atgtctttat taaaaaanaa aaaaaagggc | 1920 |
| ggccgccgac tagtga | 1936 |

<210> SEQ ID NO 2
<211> LENGTH: 637
<212> TYPE: DNA
<213> ORGANISM: Homo sapiens

<400> SEQUENCE: 2

| | |
|---|---|
| gtaggggcag acttactgcc ttgaacgaaa gacgatggtc ctcgctcagc ctcactccaa | 60 |
| ttatgttcct ctaggtgggg caggtagggg gtccagcttc ctgcttgctg gtggttcagg | 120 |
| tcatgcgtcc agccttgtcc cttctgacct gggccctacc cacggggaaa tgttcccata | 180 |
| gcagaagaat cagccccaca gtgcaggggt gtgttagtgg ggaacgggct ctgggctcct | 240 |
| gtgggaacca gggacccccct atcttggtac cggtcattgg atgtatcccc agctcatgcc | 300 |
| tgtgtctgtc ttggcccgtg tggtcaccct gtgttcatct ctctcccagc catggcctct | 360 |
| caaactgggg ttttcgtctc cctatgaggg ggtcctggta tgtacgcgtt cggtgggccc | 420 |
| gcggtgcatg tctcccggtg cagtgcatgc tggggttccc tggggccctg ggcccctcgt | 480 |
| aggatagaca gagcctgtcc taaccttccg gaagtgcatg ctggggaggc cccttgcctg | 540 |
| ctgaccttct gtgctcagga cgactaatcg gccacatgac caccactctg tcccatggga | 600 |
| ttcctagaga agtctcacta agagcccagc acactca | 637 |

<210> SEQ ID NO 3
<211> LENGTH: 2693
<212> TYPE: DNA
<213> ORGANISM: Homo sapiens
<220> FEATURE:
<221> NAME/KEY: misc_feature
<222> LOCATION: (586)..(586)
<223> OTHER INFORMATION: n=a, c, g or t
<220> FEATURE:
<221> NAME/KEY: misc_feature
<222> LOCATION: (1480)..(1480)
<223> OTHER INFORMATION: n=a, c, g or t
<220> FEATURE:
<221> NAME/KEY: misc_feature
<222> LOCATION: (1532)..(1532)
<223> OTHER INFORMATION: n=a, c, g or t
<220> FEATURE:
<221> NAME/KEY: misc_feature
<222> LOCATION: (1562)..(1566)
<223> OTHER INFORMATION: n=a, c, g or t
<220> FEATURE:
<221> NAME/KEY: misc_feature
<222> LOCATION: (1569)..(1569)
<223> OTHER INFORMATION: n=a, c, g or t
<220> FEATURE:
<221> NAME/KEY: misc_feature
<222> LOCATION: (1571)..(1571)
<223> OTHER INFORMATION: n=a, c, g or t
<220> FEATURE:
<221> NAME/KEY: misc_feature
<222> LOCATION: (1631)..(1631)
<223> OTHER INFORMATION: n=a, c, g or t
<220> FEATURE:
<221> NAME/KEY: misc_feature
<222> LOCATION: (2266)..(2512)
<223> OTHER INFORMATION: n=a, c, g or t -continued

```
<400> SEQUENCE: 3
gctcctacag ccgcatctgc gttaacatag catccctatg gccactgtct cccttgatcc      60
ccacagccat cctaggagaa aggcagaatg tcataatttg ctaaaaggga tgctgaggct     120
ctgggaggga aagggacttg cctaaagccc cagggtgaag cagcatctct ggactcccag     180
tccagtgatc ttgcccaata ctttgctgct tgcctatacc cctctaactt ggtcaacagc     240
acatcacagg gcaagcccaa tccctgcttc attttttatat atgggcgctg gtccacagcc     300
ccactctcca gccatttgga aacaaaaaca gatgctattg ttcttcctta gagaacgtgg     360
ccagtggaga cggcacactg gaaatcagag tgaatgttct tgaaagaggg tcacgggtca     420
acaaggccca gccaaaggat gcagtagaac cattttcctt agaaatcttt gggagtgaag     480
taggcttcag ccactaccca tccctgccct tgcggctacc actaccccat tagtttagac     540
agggtcgggc ggggaggggt gtggagaaga aatgagcttg cctgtngccc ccaggctccc     600
tctgtcctag ctcaggtctg ggtgccattc tttacactcg tgtgctcgct cacgcacaca     660
tcacacacct tgctggtcac acagtcacag actcgcctct gctcctgtgg tccagtggcc     720 ggacacccc tgggatggct caaaggagtc aggacttgga agtggggaca tcagggtagc     780
tgaaggaaat ccacacaccc agagcatctc ggagttcaga ctctcagacc tgaagtaggc     840
gcccccggga ctgggctagg agttggacgg aatggaggat ggaggacagc gagaagaaag     900
gaagagaaat gcaaagtgtg ggcagccgcc aagagtgaaa atagagggaa gtgtcatgca     960
agtgctggac agaaggcggc aggtgggacg agcccacag cccctcctc aaaaacgacc    1020 acctccagga ctcagtgatc cctgggggc aggctctgcc agccctcggc cacacgtggc    1080
tccggcaccc atggtcccag tgccttggat ggagacggcc agttctggcg ccagatgtg    1140 gtgctctgga atccagtccc atttccttcc tggccacgcc tgttccagcg gcctctttgg    1200
ctgcattcag cccctactta cctggggacc ccggctgggg cacaagagca ccaggggggt    1260
agggcccaaa gggatcaggg gaagcctctg gcctggaggg tatggggcac gcttccccaa    1320
gggcggaccc ggcaggagga agcccaggag ctgggtcctg ccgcccagga gctgggccct    1380
gccacccagg ccgggctagg gacatggcag ggcctgggca tcctgacgct ggacttgggc    1440
gacctgggag gcacagggag gggagagatg ggcggcccn acccagcgca gtgccggcca    1500
caccccaagg cggttgccag agcttaaggc cnggccccag caggagaaca tcccagctcc    1560
annnnnccnc nccgcagcca gtgctccttg tcaagctccc cccgtcactc caggtgggag    1620 ccacccggt nagggggtgt gccacttgcc cccagggcac tcctctgggc atcccgggtg    1680 ggggatttg gggccgtggg gggcagtctc tggtacctgt gtgcgtcagg gatgctctgc    1740
acctgcaacc aggtgtcgtc cacgggcggg ggcatgggca tggtgacagt ggtcctgttg    1800
atgtcaccga tgatgctgag cgcctccttc agcgcgtggt gcatgtgcag catctcgtcg    1860
tgctgctgtg cctgctctgc caactcctcc atcagtgtgt tctggttccc acatgagtac    1920
atattggcca gcggctccga gatgatgaac tccggggtct gagagtgggc aaacagggaa    1980
gaaggttggg acctggtgcc tgtgccgccc tggctgcctt gctgggccct tctgggactg    2040
tgcgctggac ttggagcccc ttggagtatg gcttttcaca cgggcttcta taccgcttcg    2100 actgaagat ccacctcccc actgcctttt ctcactcaga tggggacacc gaggtccaga    2160
ggaaaagaca cctgtcaaat gtcacagatc tgggagggga cttaagacct atcatgccaa    2220
gaggacacct gtctactcag ttttttttg gtggggcggg gggcgnnnnn nnnnnnnnnn    2280
nnnnnnnnnn nnnnnnnnnn nnnnnnnnnn nnnnnnnnnn nnnnnnnnnn nnnnnnnnnn    2340
```

-continued

```
nnnnnnnnnn nnnnnnnnnn nnnnnnnnnn nnnnnnnnnn nnnnnnnnnn nnnnnnnnnn      2400
nnnnnnnnnn nnnnnnnnnn nnnnnnnnnn nnnnnnnnnn nnnnnnnnnn nnnnnnnnnn      2460
nnnnnnnnnn nnnnnnnnnn nnnnnnnnnn nnnnnnnnnn nnnnnnnnnn nnggagttgg      2520
agttgatgcc tggatacagg agctctgtgg gtgggagtga gacaaaacac agggtcctga      2580
gctctgggga ccaagcaatg tcctctggtg aaaaaaatcc tggacttgct ggcagaagat      2640
ttgcctctta cttgccatgt gctctgaata catttacctg ccctctggga aaa             2693
```

<210> SEQ ID NO 4
<211> LENGTH: 292
<212> TYPE: DNA
<213> ORGANISM: Homo sapiens
<220> FEATURE:
<221> NAME/KEY: misc_feature
<222> LOCATION: (284)..(284)
<223> OTHER INFORMATION: n=a, c, g or t

<400> SEQUENCE: 4

```
aagaatatga gatttgctta gaaatgaagg actggaagga gcccacagag ttattttta       60 aactatccag taaggcttag agggtttcaa tcagaaatat gtgttagggg aaaaaatgca      120 cttttttctat attaaaaaat attattttct tcttttaaat gtaaagcatt cctattgtga     180
agaattgaga aaatacagaa aagtacaaag aaaaacatta cctacaactc caccatccgt      240
gattatcact gttcacattt gtggctcatt tttcagtatk tctnttattt aa              292
```

<210> SEQ ID NO 5
<211> LENGTH: 2694
<212> TYPE: DNA
<213> ORGANISM: Homo sapiens
<220> FEATURE:
<221> NAME/KEY: misc_feature
<222> LOCATION: (52)..(52)
<223> OTHER INFORMATION: n=a, c, g or t
<220> FEATURE:
<221> NAME/KEY: misc_feature
<222> LOCATION: (74)..(74)
<223> OTHER INFORMATION: n=a, c, g or t
<220> FEATURE:
<221> NAME/KEY: misc_feature
<222> LOCATION: (76)..(76)
<223> OTHER INFORMATION: n=a, c, g or t
<220> FEATURE:
<221> NAME/KEY: misc_feature
<222> LOCATION: (81)..(81)
<223> OTHER INFORMATION: n=a, c, g or t
<220> FEATURE:
<221> NAME/KEY: misc_feature
<222> LOCATION: (93)..(93)
<223> OTHER INFORMATION: n=a, c, g or t
<220> FEATURE:
<221> NAME/KEY: misc_feature
<222> LOCATION: (98)..(98)
<223> OTHER INFORMATION: n=a, c, g or t
<220> FEATURE:
<221> NAME/KEY: misc_feature
<222> LOCATION: (123)..(123)
<223> OTHER INFORMATION: n=a, c, g or t
<220> FEATURE:
<221> NAME/KEY: misc_feature
<222> LOCATION: (132)..(132)
<223> OTHER INFORMATION: n=a, c, g or t
<220> FEATURE:
<221> NAME/KEY: misc_feature
<222> LOCATION: (173)..(173)
<223> OTHER INFORMATION: n=a, c, g or t
<220> FEATURE:
<221> NAME/KEY: misc_feature
<222> LOCATION: (217)..(217)
<223> OTHER INFORMATION: n=a, c, g or t

```
<220> FEATURE:
<221> NAME/KEY: misc_feature
<222> LOCATION: (257)..(257)
<223> OTHER INFORMATION: n=a, c, g or t
<220> FEATURE:
<221> NAME/KEY: misc_feature
<222> LOCATION: (2539)..(2539)
<223> OTHER INFORMATION: n=a, c, g or t

<400> SEQUENCE: 5
tactatattg ctcagcattt ctaagtattc tctaagtgct ctttatttat gntttaaaat      60
agctctctta cccngntgcg ncgactagaa gancttgntt taggaaacaa tgaaatatat     120
aanttgccag antcaattgg agccctctta catctaaaag atctctggtt ggntggaaat     180
caactgtcag aattacctca ggaaatagga aatctgnaga acctgctgtg tttagatgtc     240
tctgaaaaca ggttggnaag acttcctgaa gaaatcagtg gcctgacttc attaacggat     300
ttagtcattt cccagaactt attagaaacg attccggatg gcattggaaa actaaagaaa     360
ctgtcaatct tgaaggtgga tcagaataga ctcacacagt tgcctgaagc agttggggaa     420
tgtgaaagtc tcactgagtt agttcttaca gaaaatcagc tcctgaccct gcctaaaagc     480
attggaaaac taagaagtt gagcaacttg aatgcagaca gaaataaatt agtgtcctta     540
ccaaaagaga tcggcgggtg ctgcagcctc actgtgttct gtgtacgtga caacagacta     600
actcggatac ctgcagaggt gtcacaggca acagaacttc atgtcctgga tgtggcaggg     660
aacaggttgc tgcatctacc tttatccctg actgccttga agttgaaggc tctgtggcta     720
tctgacaacc agtcccagcc cctgcttaca ttccagacag acacagacta caccacagga     780
gagaagattt taacctgtgt cttacttcct cagctgcctt ctgaacctac ttgtcaagag     840
aatctgcctc gctgtggtgc actggagaac ttggtaaatg atgtctctga tgaagcctgg     900
aacgagcgtg ctgtcaacag agtcagtgcg atccgatttg tggaggatga gaaagatgaa     960
gaagacaatg agacgagaac acttctaagg cgagccactc cacacccagg ggagttaaag    1020
cacatgaaaa agacagtgga gaatttacgg aatgacatga atgctgctaa aggactggac    1080
tcaaacaaaa acgaggtcaa tcatgccatt gaccgagtga ccacttctgt gtagagtttc    1140
acctccaagt tttacctcct gtgtcttcct ctgctgtcga gacgttcctg tctgcttccc    1200
gggagcctca cgtgctcctt gtcctaacca gcccccgcgc gccatcttcc cgtgagtgt    1260 ggggaagctg ctgtctccca ggaagtgcct tactcatccc gcaaccagtc agcgcaccag    1320
tggtctcccg gtgtgatttt tttttttttt aatttcagtt gtttgtaata agtagaatac    1380
actactgtaa acatacgacc tttgttttg tcttatgttg gggtaaagga aagcaggaag    1440 gggaatttt atcctcctcc cttccgtaaa gtgctgggat attttgaatc ccccaagttc     1500
ccttggacct actgatgaga gatagtttta tgtatgggga aaatggata ctttttaaac    1560 cttttttggc agctcagatg gtgtaaattt taaaattttg tataggtatt tcataacaaa    1620
aatatgtatt tcttttttgt tattttatct tgaaaacggt acatatttta gtatttgtgc    1680
agaaaaacaa gtcctaaagt atttgttttt atttgtacca tccacttgtg ccttactgta    1740
tcctgtgtca tgtccaatca gttgtaaaca atggcatctt tgaacagtgt gatgagaata    1800
ggaatgtggt gttttaaagc agtgttgcat tttaatcagt aatctacctg gtggatttgt    1860
ttttaaccaa aaagatgaat tatcaatgat ttgtaattat atcggttgat ttttttttgaa    1920 aagatgaacc aaaggatttg actgctaata tttattcct tacacttttt ttctgaataa     1980
gtctctcata atgagtgcag tgtcagactg tgcctactct gatggtatgt gccatttgta    2040
```

-continued

```
aaataaaata gagcagaaaa acacaaaaag agaacactgg ttcagacatt cagtgggcaa    2100
gtaaattatg gactgcaaaa taatgatttt tattcaagaa agctttaaaa gttttatatc    2160
cagatataca accacaataa agcaaaataa cctactatca aaatagaaat gttgctatct    2220
ttataagtgc aatttaattt gtaaatagag tttgaatcaa agtatcacaa aatactgctt    2280
caagatttaa ttttaaatct gctaatttaa gggatattgg gaaaagtttt ggtgtgtttc    2340
tgttgatttc ttttttgtat gctgtgataa agagaaatg aaaagtgcca gtcactgtgt    2400
ggtgtctagg aaaatcatat atattttttt ctccaagaaa taaattcatc ctggacattg    2460
gccatacagc ttttttaaaat tattactttg tatgttcaag tgatagcagg tagccaaatt    2520
ctttgacagt gtgctctgnt ctgttaaata tctaaattac ccgtcagttg tgagtgacct    2580
cctgtgggac ttgcattcac atggggcaga gcccagaatt gcctttgact ctggctagta    2640
attttgggtt gtggctatct ggccaattgg actccttata aacccgtctt caac          2694
```

```
<210> SEQ ID NO 6
<211> LENGTH: 1335
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n=a, c, g or t

<400> SEQUENCE: 6
```

```
tcatatagta ggaaganaag cacctaggtt tgaggccagg gctggctgct gtcagaacct     60
aggccctccc ctgccttgct ccacacctgg tcaggggaga gaggggagga aagccaaggg    120
aagggaccta actgaaaaca aacaagctgg gagaagcagg aatctgcgct cgggttccgc    180
agatgcagag gttgaggtgg ctgcgggact ggaagtcatc gggcagaggt ctcacagcag    240
ccaaggaacc tggggcccgc tcctccccc tccaggccat gaggattctg cagttaatcc    300
tgcttgctct ggcaacaggg cttgtagggg gagagaccag gatcatcaag gggttcgagt    360
gcaagcctca ctcccagccc tgcaggcag ccctgttcga aagacgcgg ctactctgtg     420 gggcgacgct catcgccccc agatggctcc tgacagcagc ccactgcctc aagccgtggc    480
cgctacatag ttcacctggg gcagcacaac ctccagaagg aggagggctg tgagcagacc    540
cggacagcca ctgagtcctt ccccaccccc ggcttcaaca acagcctccc caacaaagac    600
caccgcaatg acatcatgct ggtgaagatg gcatcgccag tctccatcac ctgggctgtg    660
cgacccctca ccctctcctc acgctgtgtc actgctggca ccagctgcct catttccggc    720
tggggcagca cgtccagccc ccagttacgc ctgcctcaca ccttgcgatg cgccaacatc    780
accatcattg agcaccagaa gtgtgagaac gcctacccca gcaacatcac agacaccatg    840
gtgtgtgcca gcgtgcagga agggggcaag gactcctgcc agggtgactc cggggggccct    900 ctggtctgta accagtctct tcaaggcatt atctcctggg gccaggatcc gtgtgcgatc    960
acccgaaagc tggtgtctca cacgaaagtc tgcaaatatg tggactggat ccaggagacg    1020
atgaagaaca attagactgg acccacccac cacagcccat caccctccat ttccacttgg    1080
tgtttggttc ctgttcactc tgttaataag aaaccctaag ccaagaccct ctacgaacat    1140
tctttgggcc tcctggacta caggagatgc tgtcacttaa taatcaacct ggggttcgaa    1200
atcagtgaga cctggattca aattctgcct tgaaatattg tgactctggg aatgacaaca    1260
cctggtttgt tctctgttgt atccccagcc ccaaagacag ctcctgccat atatcaagtt    1320
tcaataaata tttct                                                     1335
```

-continued

```
<210> SEQ ID NO 7
<211> LENGTH: 1079
<212> TYPE: DNA
<213> ORGANISM: Homo sapiens
<220> FEATURE:
<221> NAME/KEY: misc_feature
<222> LOCATION: (268)..(268)
<223> OTHER INFORMATION: n=a, c, g or t
<220> FEATURE:
<221> NAME/KEY: misc_feature
<222> LOCATION: (688)..(688)
<223> OTHER INFORMATION: n=a, c, g or t
<220> FEATURE:
<221> NAME/KEY: misc_feature
<222> LOCATION: (700)..(700)
<223> OTHER INFORMATION: n=a, c, g or t

<400> SEQUENCE: 7
tttttgaaga atgccctgca aggcatcaac tggaatgtgt ttattaccaa acaagacaga        60
agagaaccag ggcctgactt ggcagtggcc ccaggctgca tgggctcagg taggctcaga       120
ccggccccag gagtgggaga gcccagagaa gagggaaaaa gagtagtggc caggaggggt       180
ctggctggga catgccactc tgggccatca gcttctggat ccactcaaag tggtggctga       240
tattggtgta gacaccgggc cgattggncc gaccacagcc cactcccag ctcacgactc        300 caatctgata ccacagtcca ttcttgttac aggccaaggg tccacctgag tcaccgaagc       360
aggcatcctt cccgccttgg gcattgccag cacaaaccat gtctccaaag atgtccttgc       420
ggaaactgta cttgaggaag aggtggttgc acatagagtt gtttatgatg gcgacctgaa       480
cttcctggag ggtgtgggga gatggcagtg cctcatcctc tttgatgtac ccccagccag       540
tcacccagca gtctgtccgg ttctcaaact caaatgtgga ggcctggaga cagatgggct       600
ggatgtgttt agtgtaggtg acaggtgcag acagcttcac caaggcaatg tcatagggtg       660
aattccccag ttagcgaggg ctcagatnga tattcgatan gaagtaacgg gtgtagtagg       720
cctgcaggct ccagaaggat ggcatggaag tcagctggcc aaactggacc atccaccgg        780 agggatcact aagtcacta taggtttcaa agcagtgcgc cgccgtgagt gcccagcggt       840
ggctgagcag gctcactccg catacgtggg aatcccacag gcgcaggctc ccctgccacg       900
gccaacgccc gagttcggcg tcctctccac ccacgatgcg cgacgtgatg acccgtcggc       960
cgcatggtcc tgataagggc gccgcctcct gcgactccgg cttcctgagt ccagcccgag      1020
ccagcagcag cgccagcagc agcgccccgc gcgcgcccat ggcctcctct cccgcggtg       1079
```